United States Patent [19]
Gaugler et al.

[11] Patent Number: 5,512,437
[45] Date of Patent: Apr. 30, 1996

[54] METHOD FOR DETERMINING HEAD AND NECK SQUAMOUS CELL CARCINOMAS, PROSTATE CARCINOMAS, AND BLADDER TUMORS BY ASSAYING FOR MAGE-3

[75] Inventors: Béatrice Gaugler; Thierry Boon-Falleur; Benoit van den Eynde; Etienne DePlaen; Francis Basseur; Bernard Lethe; Pierre van der Bruggen, all of Brussels, Belgium

[73] Assignee: Ludwig Institute for Cancer Research, New York, N.Y.

[21] Appl. No.: 204,727

[22] Filed: Mar. 1, 1994

[51] Int. Cl.$^6$ .............................. C12Q 1/68; C12P 19/34; G01N 33/53; C07H 21/04
[52] U.S. Cl. .............................. 435/6; 435/6; 435/91.2; 435/7.1; 435/7.9; 536/24.3; 536/23.1
[58] Field of Search .................. 435/6, 91.2, 7.1–7.9; 536/24.3–.33, 23.1

[56] References Cited

FOREIGN PATENT DOCUMENTS

WO9220356 11/1992 WIPO.

OTHER PUBLICATIONS

Van der Bruggen, et al., "A Gene Encoding an Antigen Recognized By Cytolytic T Lymphocytes On A Human Melanoma", Science 254: 1643–1647 (Dec. 13, 1991).
Brasseur, et al., "Human gene MAGE–1, which codes for a tumor rejection antigen, is expressed by some breast tumors", Int. J. Cancer 52: 839–841 (1992).
Gaugler, et al., "Human Gene MAGE–3 Codes for an Antigen Recognized on a Melanoma by Autologous Cytolytic T Lymphocytes", J. Exp. Med. 179: 921–930 (1994).
Schreiber–"Tumor Immunology" In Fundamental Immunology, William Paul, Raven Press 1989, pp. 923–946.

*Primary Examiner*—W. Gary Jones
*Assistant Examiner*—Dianne Rees
*Attorney, Agent, or Firm*—Felfe & Lynch

[57] ABSTRACT

A method for determining head and neck squamous cell carcinomas, bladder tumors and prostate carcinomas is described. The method involves assaying for expression of the gene coding for tumor rejection antigen precursor MAGE-3, or its expression product. Various assays, and kits useful for these assays, are described.

11 Claims, No Drawings

METHOD FOR DETERMINING HEAD AND NECK SQUAMOUS CELL CARCINOMAS, PROSTATE CARCINOMAS, AND BLADDER TUMORS BY ASSAYING FOR MAGE-3

FIELD OF THE INVENTION

This invention relates to cancer diagnosis. More particularly, it relates to a so-called "tumor rejection antigen precursor" referred to as MAGE-3, which has been identified as a "marker" for certain cancers, neck and head squamous cell carcinomas, bladder tumors, and prostate carcinomas, in particular.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18:769–778 (1957); Klein et al., Cancer Res. 20: 1561–1572 (1960); Gross, Cancer Res. 3: 326–333 (1943), Basombrio, Cancer Res. 30:2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53:333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum⁻ antigen presenting cell lines are immunogenic variants obtained by mutagenesis of mouse tumor cells or cell lines, as described by Boon et al., J. Exp. Med. 152: 1184– 1193 (1980), the disclosure of which is incorporated by reference. To elaborate, tum⁻ antigens are obtained by mutating tumor cells which do not generate an immune response in syngeneic mice and will form tumors (i.e., "tum⁺" cells). When these tum⁺ cells are mutagenized, they are rejected by syngeneic mice, and fail to form tumors (thus "tum⁻"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43:125 (1983).

It appears that tum⁻ variants fail to form progressive tumors because they initiate an immune rejection process. The evidence in favor of this hypothesis includes the ability of "tum⁻" variants of tumors, i.e., those which do not normally form tumors, to do so in mice with immune systems suppressed by sublethal irradiation, Van Pel et al., Proc. Natl. Acad. Sci. USA 76: 5282–5285 (1979); and the observation that intraperitoneally injected tum⁻ cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same tum⁻ variant, even when immunosuppressive amounts of radiation are administered with the following challenge of cells (Boon et al., Proc. Natl, Acad. Sci. USA 74:272–275 (1977); Van Pel et al., supra; Uyttenhove et al., supra).

Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearson et al., Cancer Res. 48: 2975–1980 (1988) in this regard.

A class of antigens has been recognized which are presented on the surface of tumor cells and are recognized by cytolytic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., Adv. Cancer Res. 24:1–59 (1977); Boon et al., J. Exp. Med. 152:1184–1193 (1980); Brunner et al., J. Immunol. 124: 1627–1634 (1980); Maryanski et al., Eur. J. Immunol. 124:1627–1634 (1980); Maryanski et al., Eur. J. Immunol. 12: 406–412 (1982); Palladino et al., Canc. Res. 47: 5074–5079 (1987). This type of analysis is required for other types of antigens recognized by CTLs, including minor histocompatibility antigens, the male specific H-Y antigens, and the class of antigens referred to as "tum–" antigens, and discussed herein.

A tumor exemplary of the subject matter described supra is known as P815. See DePlaen et al., Proc. Natl. Acad. Sci. USA 85: 2274–2278 (1988); Szikora et al., EMBO J 9:1041–1050 (1990), and Sibille et al., J. Exp. Med. 172:35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum⁻ variants following mutagenesis, including variants referred to as P91A (DePlaen, supra), 35B (Szikora, supra), and P198 (Sibille, supra). In contrast to tumor rejection antigens—and this is a key distinction—the tum⁻ antigens are only present after the tumor cells are mutagenized. Tumor rejection antigens are present on cells of a given tumor without mutagenesis. Hence, with reference to the literature, a cell line can be tum⁺, such as the line referred to as "P1", and can be provoked to produce tum⁻ variants. Since the tum⁻ phenotype differs from that of the parent cell line, one expects a difference in the DNA of tum⁻ cell lines as compared to their tum⁺ parental lines, and this difference can be exploited to locate the gene of interest in tum⁻ cells. As a result, it was found that genes of tum⁻ variants such as P91A, 35B and P198 differ from their normal alleles by point mutations in the coding regions of the gene. See Szikora and Sibille, supra, and Lurquin et al., Cell 58:293–303 (1989). This has proved not to be the case with the TRAs of this invention. These papers also demonstrated that peptides derived from the tum⁻ antigen are presented by the $L^d$ molecule for recognition by CTLs. P91A is presented by $L^d$, P35 by $D^d$ and P198 by $K^d$.

PCT application PCT/US92/04354, filed on May 22, 1992 assigned to the same assignee as the subject application, teaches a family of human tumor rejection antigen precursor coding genes, referred to as the MAGE family. Several of these genes are also discussed in van der Bruggen et al., Science 254: 1643 (1991). It is now clear that the various genes of the MAGE family are expressed in tumor cells, and can serve as markers for the diagnosis of such tumors, as well as for other purposes discussed therein. See also Traversari et al., Immunogenetics 35:145 (1992); van der Bruggen et al., Science 254:1643 (1991). The mechanism by which a protein is processed and presented on a cell surface has now been fairly well documented. A cursory review of the development of the field may be found in Barinaga, "Getting Some 'Backbone': How MHC Binds Peptides", Science 257: 880 (1992); also, see Fremont et al., Science 257: 919 (1992); Matsumura et al., Science 257:927 (1992); Latron et al., Science 257: 964 (1992). These papers generally point to a requirement that the peptide which binds to an MHC/HLA molecule be nine amino acids long (a "nonapeptide" ), and to the importance of the first and ninth residues of the nonapeptide.

Studies on the MAGE family of genes have now revealed that, in some cases a nonapeptide is presented on the surface of tumor cells, and that the presentation of the nonapeptide requires that the presenting molecule be HLA-A1. Complexes of the MAGE-1 tumor rejection antigen (the "TRA" or nonapeptide" ) leads to lysis of the cell presenting it by cytolytic T cells ("CTLs" ). Additional research has correlated other nonapeptides derived from MAGE and genes to HLA-A1 and other MHC class I molecules.

Research presented in, e.g., U.S. patent application Ser. No. 07/938,334 filed Aug. 31, 1992, showed that, when comparing homologous regions of various MAGE genes to the region of the MAGE- 1 gene coding for the relevant nonapeptide, there is a great deal of homology.

The nucleic acid sequences which code for the nonapeptides were also described therein. These nucleic acid sequences were described as also being useful as diagnostic probes for tumor presence.

The application also showed how it had been found that a cellular model could be used, wherein a non-human cell can be transfected with a nucleic acid sequence coding for a human HLA molecule. The resulting transfectant could then be used to test for nonapeptide specificity of the particular HLA molecule, or as the object of a second transfection with a MAGE gene. The cotransfectant could be used to determine whether the particular MAGE based TRA is presented by the particular HLA molecule.

Many of the references referred to supra present data on the expression pattern of various MAGE genes in different types of cell lines and tumor tissues. What is evident from these data is that there is no "unifying principle" which allows one to predict which MAGE gene will be expressed by a particular tumor type. Thus, while on one level one can say that MAGE genes are "markers" for tumors, on the level of specific tumor types, the correlation of marker and tumor type is not predictable, and must be determined empirically.

This invention relates to the identification of expression of the MAGE-3 gene in head and neck squamous cell carcinomas, bladder tumors, and prostate tumors. Methods for determining presence of these conditions, and reagents useful in the assays, are the subject matter of the invention.

DETAILED DESCRIPTION OF PREFERRED EMBODIMENTS

Example

The expression of the MAGE-3 gene in various tumors and normal tissues was evaluated, using both reverse transcription and polymerase chain reaction ("PCR" ) amplification. To perform these assays, the total RNA of the cells of interest was extracted via the well known guanidine-isothiocyanate procedure of Davis et al., Basic Methods in Molecular Biology, 1986 (New York, Elsevier, pp. 130), which is incorporated by reference in its entirety. cDNA was then synthesized, by taking 2 ug of the RNA, diluting it with water, and then adding the following materials: 4 ul of 5X reverse transcriptase buffer, 1 ul each of each dNTP (10 mM), 2 ul of a 20 µM solution of oligo dT, 20 units of RNAsin, 2 ul of 0.1M dithiothreitol, and 200 units of MoMLV reverse transcriptase. All materials were mixed in a 20 ul reaction volume, and incubated at 42° C. for 60 minutes. For the amplification reaction, 1/20 of the cDNA reaction product was supplemented with 5 ul of PCR buffer, 0.5 ul of each of the dNTPs (10 mM), 1 ul each of 20 µM solutions of primer (see infra), and 1.25 units of Taq polymerase. Water was added to a final volume of 50 uls. The primers used for MAGE-3 were:

5'-TGGAGGACCAGAGGCCCCC-3' (SEQ ID NO: 1)

5'-GGACGATTATCAGGAGGCCTGC-3' (SEQ ID NO: 2)

These correspond to a sense sequence in exon 2 of the gene (SEQ ID NO: 1), and an antisense sequence for exon 3 (SEQ ID NO: 2).

PCR was performed for 30 cycles (one minutes at 94° C., four minutes at 72° C.). PCR product was size fractionated on a 1% agarose gel, and then analyzed. The results are presented in the table which follows. These data confirm some results obtained previously, but also show the expression of MAGE-3 in head and neck squamous cell carcinomas, a result not suggested by previous work.

TABLE 1

Expression of gene MAGE-3 by tumoral, normal and fetal tissues.

| | TUMORS | |
| --- | --- | --- |
| | Number of MAGE-3 positive tumors* | |
| HISTOLOGICAL TYPE | cell lines | tumors samples |
| Melanomas | 50/62 (81%) | 72/105 (69%) |
| Head and neck squanous cell carcinomas | — | 20/36 (56%) |
| Lung carcinomas | | |
| NSCLC ‡ | 1/2 | 14/46 (30%) |
| SCLC | 18/22 (82%) | 2/3 |
| Colorectal carcinomas | 5/16 | 5/31 (16%) |

TABLE 1-continued

Expression of gene MAGE-3 by tumoral, normal and fetal tissues.

| | | |
|---|---|---|
| Mammary carcinomas | 2/6 | 16/132 (12%) |
| Bladder tumors | — | 2/6 |
| Sarcomas | 1/4 | 3/10 |
| Prostatic carcinomas | — | 3/20 |
| Renal carcinomas | 0/5 | 0/38 |
| Leukemias | 2/6 | 0/20 |
| Lymphomas | 0/6 | 0/5 |

NORMAL TISSUES

| HISTOLOGICAL TYPE | MAGE-3 expression* |
|---|---|
| ADULT TISSUES | |
| Brain | − |
| Colon | − |
| Stomach | − |
| Liver | − |
| Spleen | − |
| Skin | − |
| Lung | − |
| Kidney | − |
| Breast | − |
| Testis | ++ |
| FETAL TISSUES | |
| Brain | − |
| Liver | − |
| Spleen | − |

*Expression of gene MAGE-3 was tested by RT-PCR amplification on total RNA, with the primers described in methods. These primers distinguish MAGE-3 from the 11 other MAGE genes that have been identified.
‡ NSCLC are non-small cell lung carcinomas, SCLC are small cell lung carcinomas.

The foregoing example shows that expression of MAGE-3 is correlated to head and neck squamous cell carcinomas, bladder tumors, and prostate carcinomas. One aspect of the invention, then, is a method for determining these squamous cell carcinomas by assaying a sample for expression of MAGE-3. As MAGE genes are nearly without exception expressed only by tumor cells, there can be no question but that MAGE-3 expression is indicative of cancer. The fact that the cancer is of the squamous cell type is easily ascertainable, as squamous cells have distinct morphologies which are identifiable by the skilled artisan. Similarly, the fact that the tumor of interest is a neck or head squamous cell carcinoma as compared to a tumor from a different body part is self evident; one does not find head or neck squamous cell carcinoma in, e.g., large intestine tissue.

The assay for MAGE-3 can take many forms. Most preferably, the assay is done via determining gene expression, such as by determining mRNA transcription products. For example, amplification protocols, including but not being limited to polymerase chain reaction (PCR), and ligase chain reaction (LCR), are preferred. The assay can also be carried out using nucleic acid molecule probes, which are labelled or unlabelled, and which specifically hybridize to sequences characteristic of MAGE-3. Labelling nucleotide probes is well known to the art, labels including radioactive, fluorescent, chromophoric, magnetic, and other identifiable materials. Antibodies, haptens such as biotin, (strept)avidin, digoxin, digoxigenin, and so forth, can all be used. Non-labelled probes can also be used. In such a case, the probes will form a double stranded molecule with their target. Any remaining single stranded material can be enzymatically digested, and when something remains, it is a sign of MAGE-3 expression. For the case of polymerase chain reaction or other methodologies where a primer or primers are required, the molecules represented by SEQ ID NO: 1 and SEQ ID NO: 2 are especially preferred. Similarly, these molecules are preferred as probes.

One may also assay for the expression product of MAGE-3, i.e., the tumor rejection antigen precursor protein, via assays such as immunoassays.

The nucleotide molecules of SEQ ID NO: 1 and SEQ ID NO: 2, in isolated form, constitute another feature of this invention. They can be used alone, in combination in a one pot reagent, or in the form of a kit. In this kit aspect of the invention, separate samples of each of the nucleic acid molecules are presented in separate container means. The two components are themselves contained in a large container means, such as a box, "blister pack", and so forth. The kit may contain additional reagents which are useful in an assay. For example, a kit suited for PCR would include a polymerase, such as Taq polymerase, where an amplification kit might include T7 polymerase instead. These are optional features, however, and should not be seen as distracting from the invention as elaborated upon supra.

Other aspects of the invention will be clear to the skilled artisan and need not be adumbrated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Method for screening for possible presence of cancer, wherein said cancer is selected from the group consisting of head squamous cell carcinoma, neck squamous cell carcinoma, and prostate carcinoma, comprising assaying a tissue sample taken from the head, neck or prostate gland of a subject believed to have a head squamous cell carcinoma, a neck squamous cell carcinoma or a prostate carcinoma, and determining expression of mRNA for a MAGE-3 gene, as a determination of possible presence of said cancer in said subject.

2. The method of claim 1, comprising determining said expression by in vitro amplification of said mRNA.

3. The method of claim 2, wherein said in vitro amplification is polymerase chain reaction.

4. The method of claim 1, comprising determining expression of said mRNA with a labelled nucleodtide probe which specifically hybridizes to said mRNA.

5. The method of claim 3, further comprising carrying out said polymerase chain reaction with at least one primer selected from the group consisting of SEQ ID NO:1 and SEQ ID NO:2.

6. The method of claim 4, wherein said labelled nucleotide probe is a labelled nucleic acid molecule selected from the group consisting of SEQ ID NO:1 and SEQ ID NO: 2.

7. Method for screening for possible presence of cancer, wherein said cancer is selected from the group consisting of head squamous cell carcinoma, neck squamous cell carcinoma, and prostate cancer, comprising assaying a tissue sample taken from the head, neck or prostate gland of a subject believed to have a head squamous cell carcinoma, a neck squamous cell carcinoma or a prostate carcinoma and determining expression of MAGE-3 protein, as a determination of possible presence of said cancer in said subject.

8. The method of 7, comprising determining expression of MAGE-3 protein by immunoassay.

9. Isolated nucleic acid molecule selected from the group consisting of SEQ ID NO:1, and SEQ ID NO:2.

10. Kit useful in determining expression of mRNA for MAGE-3 gene in a cell sample, comprising separated portions of each of SEQ ID NO:1 and SEQ ID NO:2, and a means for containing both of said separate nucleic acid molecules.

11. The kit of claim 10, further comprising a separate portion of a polymerase.

\* \* \* \* \*

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
TGGAGGACCA GAGGCCCCC                                    1 9
```

( 2 ) INFORMATION FOR SEQ ID NO: 2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:
```
GGACGATTAT CAGGAGGCCT GC                    22
```